United States Patent
Hamlekhan et al.

(10) Patent No.: US 11,272,946 B2
(45) Date of Patent: Mar. 15, 2022

(54) FLUID FITTING FOR DILATION INSTRUMENT

(71) Applicant: Acclarent, Inc., Irvine, CA (US)

(72) Inventors: Azhang Hamlekhan, Irvine, CA (US); John H. Thinnes, Jr., Mission Viejo, CA (US); George L. Matlock, Pleasanton, CA (US)

(73) Assignee: Acclarent, Inc., Irvine, CA (US)

( * ) Notice: Subject to any disclaimer, the term of this patent is extended or adjusted under 35 U.S.C. 154(b) by 154 days.

(21) Appl. No.: 16/247,739

(22) Filed: Jan. 15, 2019

(65) Prior Publication Data

US 2019/0274701 A1    Sep. 12, 2019

Related U.S. Application Data (60) Provisional application No. 62/640,598, filed on Mar. 9, 2018.

(51) Int. Cl.
*A61B 17/24* (2006.01)
*A61B 1/32* (2006.01)
(Continued)

(52) U.S. Cl.
CPC ............... *A61B 17/24* (2013.01); *A61B 1/32* (2013.01); *A61M 25/0041* (2013.01);
(Continued)

(58) Field of Classification Search
CPC .............. A61M 25/10; A61M 25/1018; A61M 25/10184; A61M 25/1025; A61M 3/0295;
(Continued)

(56) References Cited

U.S. PATENT DOCUMENTS

| 4,119,099 A | * | 10/1978 | Patel ................ A61M 25/1025 604/100.01 |
| 4,123,091 A | * | 10/1978 | Cosentino .......... F16L 37/0847 285/39 |

(Continued)

FOREIGN PATENT DOCUMENTS

WO    WO 2013/016056 A2    1/2013

OTHER PUBLICATIONS

U.S. Appl. No. 62/640,598, entitled "Fluid Fitting for Dilation Instrument," filed Mar. 9, 2018.

(Continued)

*Primary Examiner* — Dianne Dornbusch
(74) *Attorney, Agent, or Firm* — Frost Brown Todd LLC (57) ABSTRACT

An apparatus includes an elongate shaft, a dilation balloon, and a fitting member. The elongate shaft includes an inflation lumen, an irrigation lumen, and at least one irrigation opening. The at least one irrigation opening is in fluid communication with the irrigation lumen. The dilation balloon is at the distal portion of the shaft. The dilation balloon is in fluid communication with the inflation lumen. The fitting member is at the proximal end of the shaft. The fitting member includes an inflation fluid port, an irrigation fluid port, and a blocking structure. The inflation fluid port is in fluid communication with the inflation lumen. The irrigation fluid port is in fluid communication with the irrigation lumen. The blocking structure is adjacent to the irrigation fluid port and defines a gap around the irrigation fluid port.

16 Claims, 7 Drawing Sheets

(51) Int. Cl.
*A61M 25/10* (2013.01)
*A61M 25/00* (2006.01)
*A61M 29/02* (2006.01)
A61B 17/00 (2006.01)

(52) U.S. Cl.
CPC .. *A61M 25/1002* (2013.01); *A61M 25/10184* (2013.11); *A61M 29/02* (2013.01); *A61B 17/00234* (2013.01); *A61B 2217/007* (2013.01)

(58) Field of Classification Search
CPC ........ A61M 3/0283; A61M 2025/0004; A61M 2025/1061; A61M 25/0067; A61M 25/0097; A61M 2210/0681; A61M 2210/0618; A61M 29/00; A61M 2039/1094; A61M 25/0014; A61M 25/104; A61M 39/10; A61B 17/24; A61B 1/233; A61B 2562/226; A61B 17/00234
See application file for complete search history.

(56) References Cited

U.S. PATENT DOCUMENTS

| | | | | |
|---|---|---|---|---|
| 4,776,841 A * | 10/1988 | Catalano | ........... | A61M 25/0026 604/43 |
| 5,035,686 A * | 7/1991 | Crittenden | ............ | A61M 25/09 604/103.05 |
| 5,047,021 A * | 9/1991 | Utterberg | ................ | F16L 33/24 604/533 |
| 5,352,215 A * | 10/1994 | Thome | .................. | A61M 39/10 604/284 |
| 6,096,011 A * | 8/2000 | Trombley, III | ....... | A61M 39/14 251/149 |
| 6,423,053 B1 * | 7/2002 | Lee | .................... | A61M 39/1011 604/523 |
| 7,878,553 B2 * | 2/2011 | Wicks | ..................... | F16L 37/38 285/319 |
| 8,951,225 B2 * | 2/2015 | Evard | .................... | A61M 29/02 604/96.01 |
| D737,436 S * | 8/2015 | Lev | .............................. | D24/129 |
| 9,095,646 B2 | 8/2015 | Chow et al. | | |
| 9,155,492 B2 | 10/2015 | Jenkins et al. | | |
| 2003/0120256 A1 * | 6/2003 | Lary | ..................... | A61M 25/00 604/509 |
| 2004/0030289 A1 * | 2/2004 | Vitullo | ............... | A61B 17/3401 604/164.01 |
| 2005/0059958 A1 * | 3/2005 | Lessard | ............. | A61M 25/0009 604/533 |
| 2005/0251246 A1 * | 11/2005 | Dubrul | ................ | A61M 25/104 623/1.42 |
| 2008/0183128 A1 | 7/2008 | Morriss et al. | | |
| 2008/0287919 A1 | 11/2008 | Kimball | | |
| 2008/0318456 A1 * | 12/2008 | Yow | ....................... | F16L 37/248 439/157 |
| 2011/0004057 A1 | 1/2011 | Goldfarb et al. | | |
| 2011/0046654 A1 * | 2/2011 | Kuppurathanam | . | A61M 25/104 606/198 |
| 2013/0184683 A1 * | 7/2013 | Chow | ................... | A61M 29/00 604/514 |
| 2014/0025036 A1 * | 1/2014 | Bierman | ........... | A61M 25/0097 604/506 |
| 2014/0074141 A1 | 3/2014 | Johnson et al. | | |
| 2014/0364725 A1 | 12/2014 | Makower | | |
| 2015/0105815 A1 * | 4/2015 | Horn | ...................... | A61M 29/02 606/192 |
| 2015/0230809 A1 * | 8/2015 | Becker | ................ | A61B 1/00165 600/435 |
| 2015/0231378 A1 * | 8/2015 | Pepper | ............ | A61M 25/10184 606/194 |
| 2016/0008083 A1 | 1/2016 | Kesten et al. | | |
| 2016/0015932 A1 * | 1/2016 | Catudal | ............... | A61M 25/008 604/164.01 |
| 2016/0038321 A1 * | 2/2016 | Shumer | ............. | A61M 25/0026 623/1.11 |
| 2016/0045708 A1 * | 2/2016 | Westhoff | ........... | A61M 25/0097 604/535 |
| 2017/0120020 A1 | 5/2017 | Lin et al. | | |
| 2018/0093085 A1 * | 4/2018 | Burkholz | .......... | A61M 25/0606 |
| 2019/0022357 A1 * | 1/2019 | Burkholz | .......... | A61M 25/0097 |
| 2019/0022367 A1 * | 1/2019 | Burkholz | .......... | A61M 25/0606 |
| 2019/0099526 A1 * | 4/2019 | Hajishah | .............. | A61M 1/008 |
| 2019/0321599 A1 * | 10/2019 | Burkholz | ............. | A61M 39/10 |
| 2020/0023166 A1 * | 1/2020 | Burkholz | .......... | A61M 25/0097 |
| 2021/0162193 A1 * | 6/2021 | Picthall | ................ | A61J 15/0053 |

OTHER PUBLICATIONS

U.S. Appl. No. 62/555,841, entitled "Adjustable Instrument for Dilation of anatomical Passageway," filed Sep. 8, 2017.
U.S. Appl. No. 15/852,470, entitled "Dilation Instrument with Guide Catheter Type Sensor," filed Dec. 22, 2017.
U.S. Appl. No. 15/852,530, entitled "Reusable Navigation Guidewire," filed Dec. 22, 2017.
U.S. Appl. No. 15/861,959, entitled "navigation Guidewire with Interlocked Coils," filed Jan. 4, 2018.
International Search Report and Written Opinion dated Jun. 26, 2019 for Application No. PCT/IB2019/051962, 10 pgs.

* cited by examiner

FLUID FITTING FOR DILATION INSTRUMENT

PRIORITY

This application claims priority to U.S. Provisional Pat. App. No. 62/640,598, entitled "Fluid Fitting for Dilation Instrument," filed Mar. 9, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

While several systems and methods have been made and used in ENT procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Dilation Instrument System

FIGS. 1A-1D show an exemplary dilation instrument system (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument system (10) of this example comprises a guidewire power source (12), an inflation fluid source (14), an irrigation fluid source (16), and a dilation instrument (20). In some versions, guidewire power source (12) comprises a source of light. In some other versions, guidewire power source (12) is part of an image guided surgery (IGS) system. Inflation fluid source (14) may comprise a source of saline or any other suitable source of fluid. Irrigation fluid source (16) may also comprise a source of saline or any other suitable source of fluid.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22).

A guide catheter (60) extends distally from handle body (22). Guide catheter (60) includes an open distal end (62) and a bend (64) formed proximal to open distal end (62). In some versions, dilation instrument (20) is configured to removably receive several different kinds of guide catheters (60), each guide catheter (60) having a different angle formed by bend (64). Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

By way of further example only, guide catheter (60) may be configured and operable in accordance with at least some of the teachings of U.S. patent application Ser. No. 15/852,470, entitled "Dilation Instrument with Guide Catheter Type Sensor," filed Dec. 22, 2017, now abandoned, the disclosure of which is incorporated by reference herein; U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein; and/or U.S. Pat. App. No. 62/555,841, entitled "Adjustable Instrument for Dilation of Anatomical Passageway," filed Sep. 8, 2017, the disclosure of which is incorporated by reference herein.

Figure 1A:
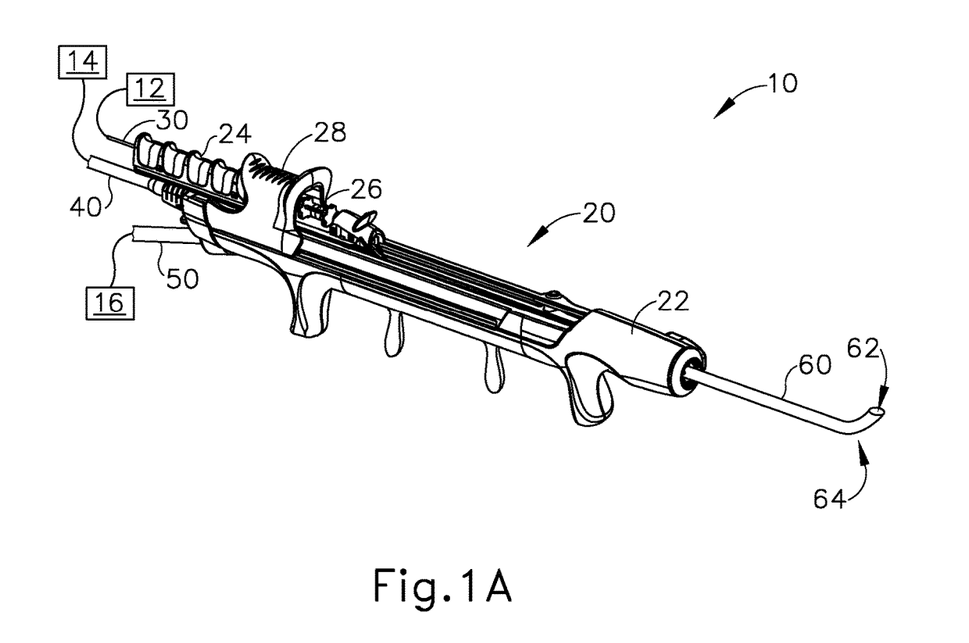
FIG. 1A depicts a perspective view of an exemplary dilation instrument system including a dilation instrument having a guidewire and a dilation catheter, showing the guidewire in a proximal position, and the dilation catheter in a proximal position.
Figure 1B:
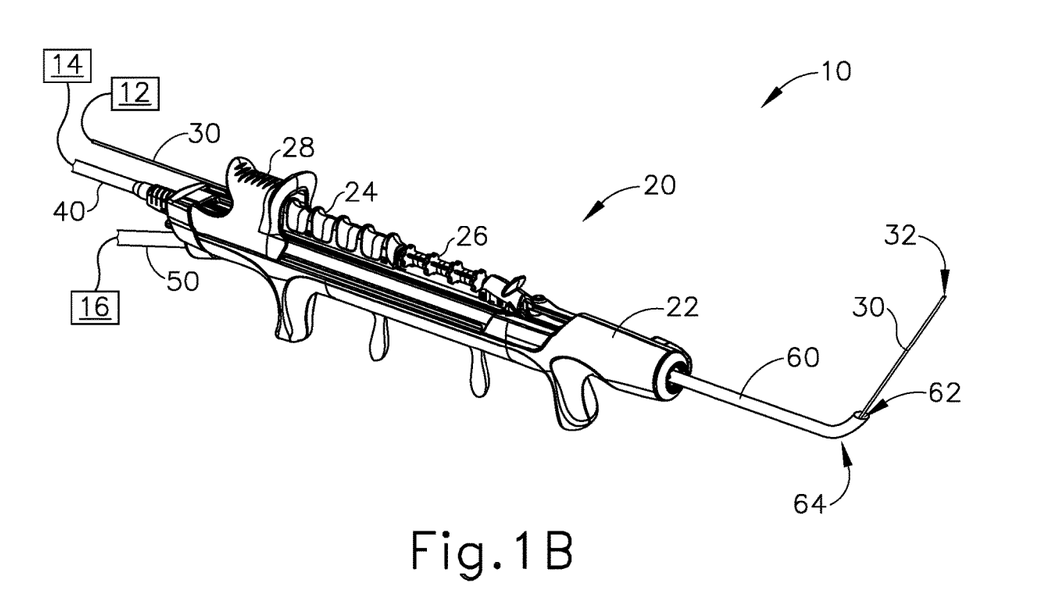
FIG. 1B depicts a perspective view of the dilation instrument system of FIG. 1A, showing the guidewire in a distal position, and the dilation catheter in the proximal position.

A guidewire (30) is coaxially disposed in guide catheter (60). Guidewire slider (24) is secured to guidewire (30). Translation of guidewire slider (24) relative to handle body (22) from a proximal position (FIG. 1A) to a distal position (FIG. 1B) thus causes corresponding translation of guidewire (30) relative to handle body (22) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

By way of further example only, guidewire (30) may be configured and operable in accordance with at least some of the teachings of U.S. patent application Ser. No. 15/861,959, entitled "Navigation Guidewire with Interlocked Coils," filed Jan. 4, 2018, issued as U.S. Pat. No. 10,610,308 on Apr. 7, 2020, the disclosure of which is incorporated by reference herein; U.S. Pat. No. 9,155,492, entitled "Sinus Illumination Lightwire Device," issued Oct. 13, 2015, the disclosure of which is incorporated by reference herein; U.S. patent application Ser. No. 15/852,530, entitled "Reusable Navigation Guidewire," filed Dec. 22, 2017, published as U.S. Pub. No. 2019/0192177 on Jun. 27, 2019, the disclosure of which is incorporated by reference herein; U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein; and/or U.S. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

Figure 1C:
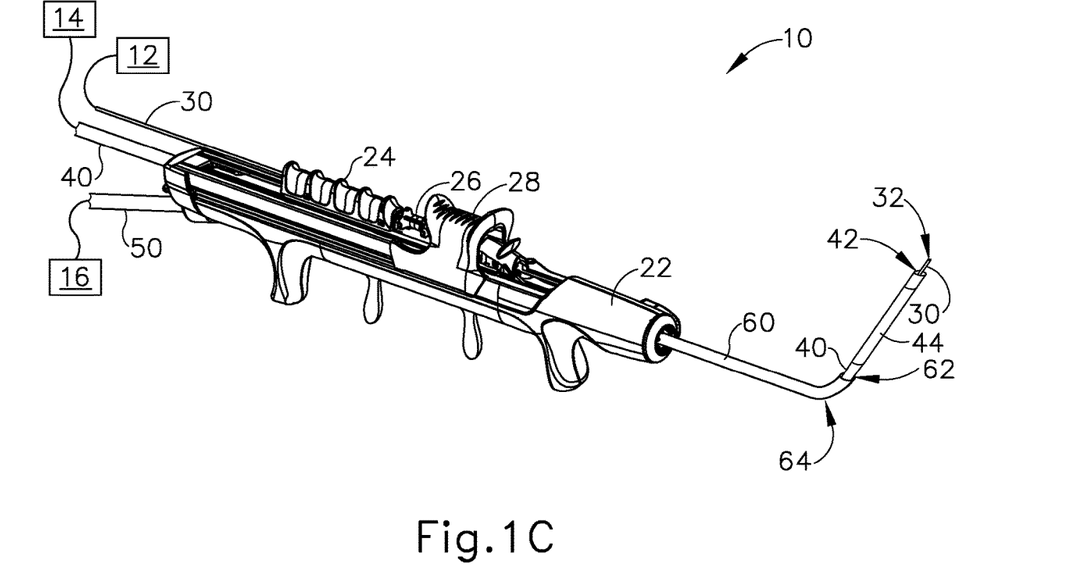
FIG. 1C depicts a perspective view of the dilation instrument system of FIG. 1A, showing the guidewire in the distal position, the dilation catheter in a distal position, and a dilator in a non-dilated state.
Figure 1D:
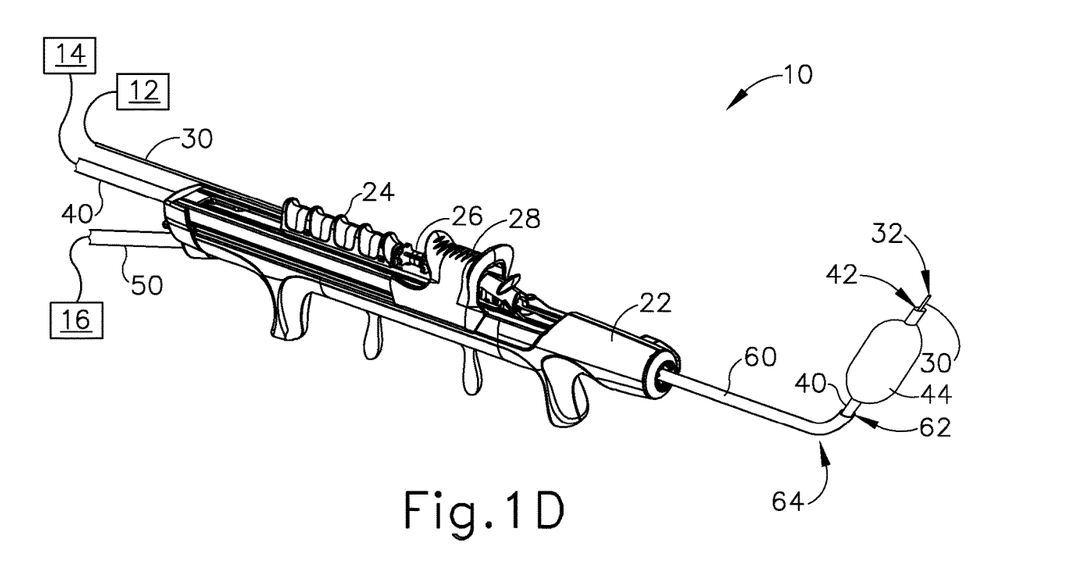
FIG. 1D depicts a perspective view of the dilation instrument system of FIG. 1A, showing the guidewire in the distal position, the dilation catheter in the distal position, and the dilator in a dilated state.

A dilation catheter (40) is coaxially disposed in guide catheter (60). Dilation catheter slider (28) is secured to dilation catheter (40). Translation of dilation catheter slider (28) relative to handle body (22) from a proximal position (FIG. 1B) to a distal position (FIG. 1C) thus causes corresponding translation of dilation catheter (40) relative to handle body (22) from a proximal position (FIG. 1B) to a distal position (FIG. 1C). When dilation catheter (40) is in a distal position, a distal portion of dilation catheter (40) protrudes distally from open distal end (62) of guide catheter (60). Dilation catheter (40) of the present example comprises a non-extensible balloon (44) located just proximal to open distal end (42) of dilation catheter (40). Balloon (44) is in fluid communication with inflation fluid source (14). Inflation fluid source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In the non-inflated state, balloon (44) is configured to be inserted into a constricted anatomical passageway (e.g., paranasal sinus ostium, Eustachian tube, etc.). In the inflated state, balloon (44) is configured to dilate the anatomical passageway in which balloon (44) is inserted. Other features and operabilities that may be incorporated into dilation catheter (40) will be described in greater detail below.

In some versions, inflation fluid source (14) comprises a manually actuated source of pressurized fluid. In some such versions, the manually actuated source of pressurized fluid may be configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after a dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via irrigation tube (50), to enable irrigation of the anatomical site in the patient. By way of example only, a dedicated irrigation catheter may be configured and operable in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein.

II. Exemplary Dilation Catheter with Integral Irrigation Feature

Figure 2:
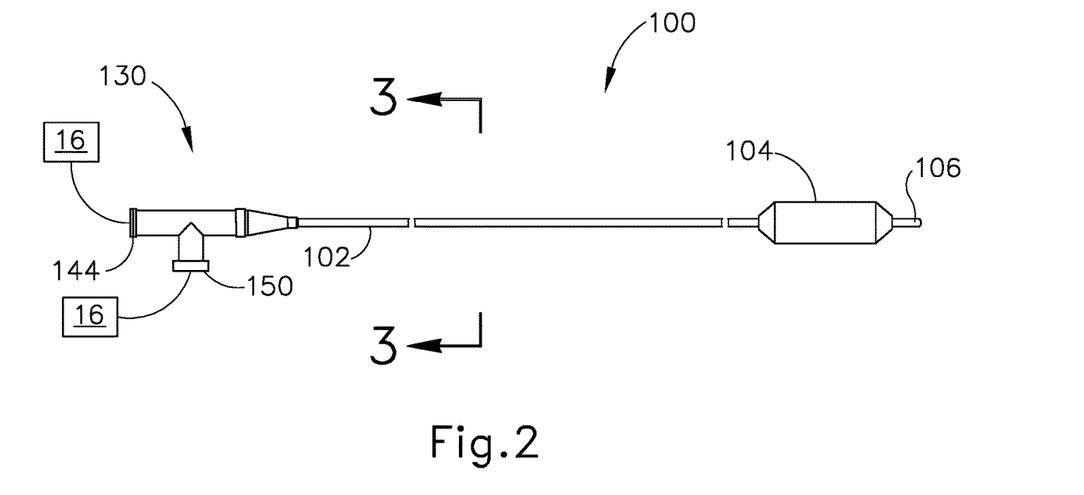
FIG. 2 depicts a side elevational view of an exemplary alternative dilation catheter that may be used in the dilation instrument system of FIG. 1A.
Figure 3:
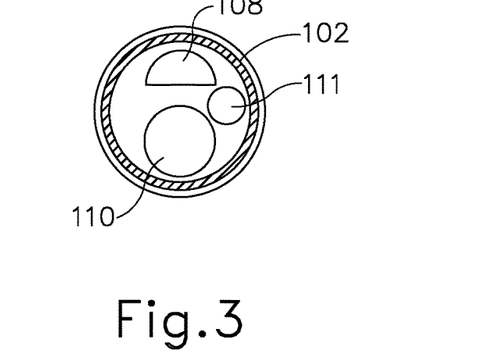
FIG. 3 depicts a cross-sectional end view of the dilation catheter of FIG. 2, taken along line 3-3 of FIG. 2.
Figure 4:
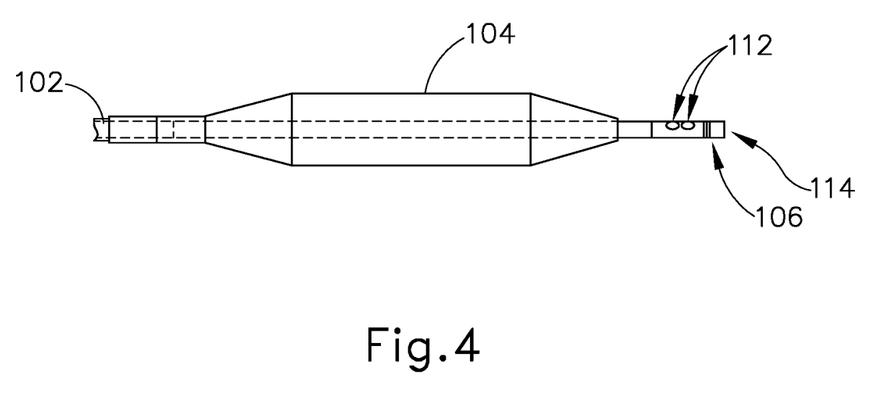
FIG. 4 depicts an enlarged side elevational view of a distal portion of the dilation catheter of FIG. 2.

As noted above, it may be desirable in some scenarios to provide irrigation at an anatomical site as part of use of instrument (20). As also noted above, this may be carried out by replacing dilation catheter (40) with a dedicated irrigation catheter. As an alternative, it may be desirable to provide a version of dilation catheter (40) that is capable of providing dilation and irrigation, thereby eliminating the need for extra steps of withdrawing dilation catheter (40) and inserting a dedicated irrigation catheter. FIGS. 2-4 show an example of a dilation catheter (100) that is capable of providing dilation and irrigation. Dilation catheter (100) may be readily used in instrument (20) in place of dilation catheter (40) described above. Except as otherwise provided below, and by way of example only, dilation catheter (100) may be constructed and operable in accordance with at least some of the teachings of U.S. Pat. No. 9,095,646, entitled "Devices and Methods for Transnasal Dilation and Irrigation of the Sinuses," issued Aug. 4, 2015, the disclosure of which is incorporated by reference herein.

Dilation catheter (100) of the present example comprises shaft (102). A dilation balloon (104) and an irrigation tip (106) are located at a distal end of shaft (102), with irrigation tip (106) being distal to balloon (104). A fluid fitting member (130) is located at the proximal end of shaft (1102). Fluid fitting member (130) includes an irrigation fluid port. (144) and an inflation fluid port. (150). As shown in FIG. 2, irrigation fluid port (144) is in fluid communication with irrigation fluid source (16); and inflation fluid port (150) is in fluid communication with inflation fluid source (14). Ports (144, 150) of the present example comprise conventional female luer fittings, such that irrigation fluid port (144) may be coupled with irrigation fluid source (16) via a conventional male leer fitting; and inflation fluid port (150) may be coupled with inflation fluid source (14) via a conventional male luer fitting.

As shown in FIG. 3, shaft (102) has adjacent multi-lumen (108, 110) tubing, which includes lumens (108, 110) that are next to each other but are spaced apart from each other, such that lumens (108, 110) are fluidly isolated from each other. An inflation lumen (108) is in fluid communication with balloon (104) and inflation fluid port (150), such that inflation lumen (108) and inflation fluid port (150) cooperate to provide a fluid pathway between inflation fluid source (14) and balloon (104). Various suitable ways in which inflation fluid port (150) may be coupled with inflation lumen (108) will be apparent to those of ordinary skill in the art in view of the teachings herein. An irrigation lumen (110) is in fluid communication with irrigation tip (106) and irrigation fluid port (144), such that irrigation lumen (110) and irrigation fluid port (144) cooperate to provide a fluid pathway between irrigation fluid source (16) and irrigation tip (106). Various suitable ways in which irrigation fluid port (144) may be coupled with irrigation lumen (110) will be apparent to those of ordinary skill in the art in view of the teachings herein. Just as lumens (108, 110) are in fluid isolation from each other, ports (144, 150) are also in fluid isolation from each other in the present example.

As also shown in FIG. 3, shaft (102) includes a guidewire lumen (111), which is configured to slidably receive guidewire (30). In the present example, irrigation lumen (110) and guidewire lumen (111) merge together in the distal portion of shaft assembly (120), thereby allowing guidewire (30) to exit distally through irrigation tip (106), In some other versions, a separate guidewire lumen (ill) is omitted, and guidewire (30) may simply be inserted through irrigation fluid port (144) to pass through irrigation lumen (110) and exit distally through irrigation tip (106). In such versions, irrigation fluid source (16) may be decoupled from irrigation fluid port (144) while guidewire (30) is disposed in irrigation lumen (110). After the operator is finished using guidewire (30), the operator may remove guidewire (30) from irrigation lumen (110), couple irrigation fluid source (16) with irrigation lumen (110), then dispense irrigation fluid from irrigation fluid source (16) to irrigation lumen (110) via irrigation fluid port (144) as needed.

As shown in FIG. 4, irrigation tip (106) includes a distally-facing tip opening (114) and a plurality of radially-facing openings (112). Openings (112, 114) are in fluid communication with irrigation lumen (110). Radially-facing openings (112) may be configured to provide a flow through openings (112) at an angle of approximately 90° from the flow through tip opening (114); at an angle of approximately 30°, 45°, or 60° degrees from the flow through tip opening (114); or at any suitable angle relative to the flow through tip opening (114). Radially-facing openings (112) may be provided in a straight linear arrangement, in a helical arrangement, and/or in any other suitable arrangement. Radially-facing openings (112) may be circular or non-circular (e.g., oval shaped, elongate slot shaped, etc.). In some versions, radially-facing openings (112) are arranged and configured to create a vortex in fluid that is expelled through openings (112).

In the present example, irrigation fluid that is communicated from irrigation fluid source (16) through irrigation fluid port (144) and through irrigation lumen (110) will ultimately exit irrigation tip (106) through openings (112, 114). Dilation catheter (100) may thus be used to dilate an anatomical passageway with balloon (104); then irrigate an adjacent cavity via irrigation tip (106). For instance, balloon (104) may be used to dilate a paranasal sinus ostium; and then irrigation tip (106) may be used to irrigate the associated sinus cavity. Irrigation tip (106) may be used to deliver irrigation fluid before, during, or after dilation of the anatomical passageway. In some variations, instead of delivering irrigation fluid through the irrigation lumen (1.10), a vacuum may be applied and a culture may be obtained by suctioning through tip opening (114) and/or radially-facing openings (112).

III. Exemplary Alternative Fluid Fitting Member for Dilation Catheter with Integral Irrigation Feature As noted above, fluid fitting member (130) of dilation catheter includes irrigation fluid port (144) and inflation fluid port (150), which are both in the form of conventional female luer fittings. There may be instances where an operator may mistakenly couple irrigation fluid source (16) with inflation fluid port (150); and inflation fluid source (14) with irrigation fluid port (144). This may be undesirable for various reasons as will be apparent to those of ordinary skill in the art in view of the teachings herein. It may still be desirable to provide fluid ports in the form of conventional female luer fittings; and also provide a dilation catheter that is capable of providing dilation and irrigation. However, it may be desirable to provide such functionality while avoiding the risk of an operator mistakenly coupling irrigation fluid source (16) with inflation fluid port (150); and inflation fluid source (14) with irrigation fluid port (144).

Figure 5A:
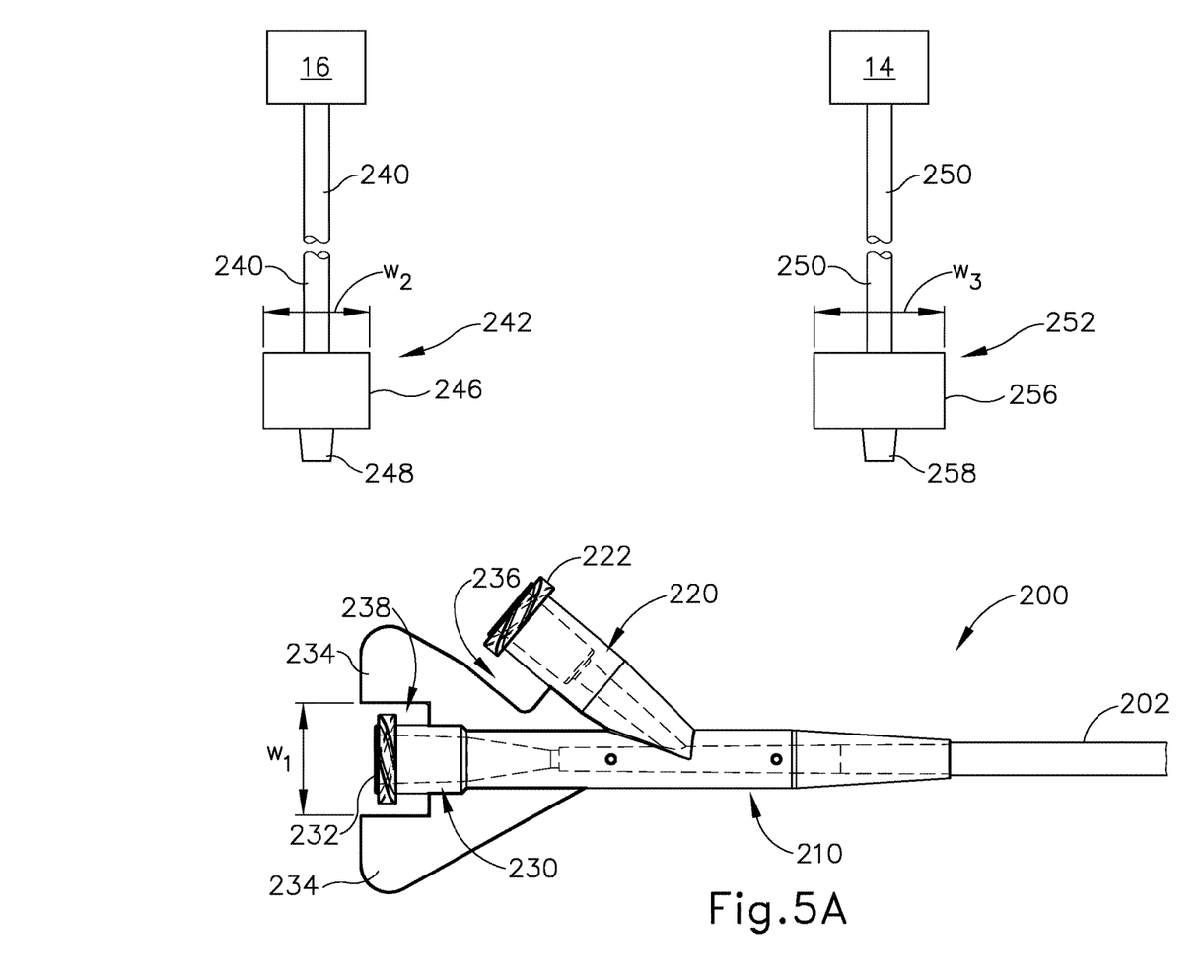
FIG. 5A depicts a top plan view of another exemplary alternative dilation catheter that may be used in the dilation instrument system of FIG. 1A, with an irrigation fluid source fitting decoupled from a fluid fitting member of the dilation catheter, and with an inflation fluid source fitting decoupled from the fluid fitting member of the dilation catheter.
Figure 5B:
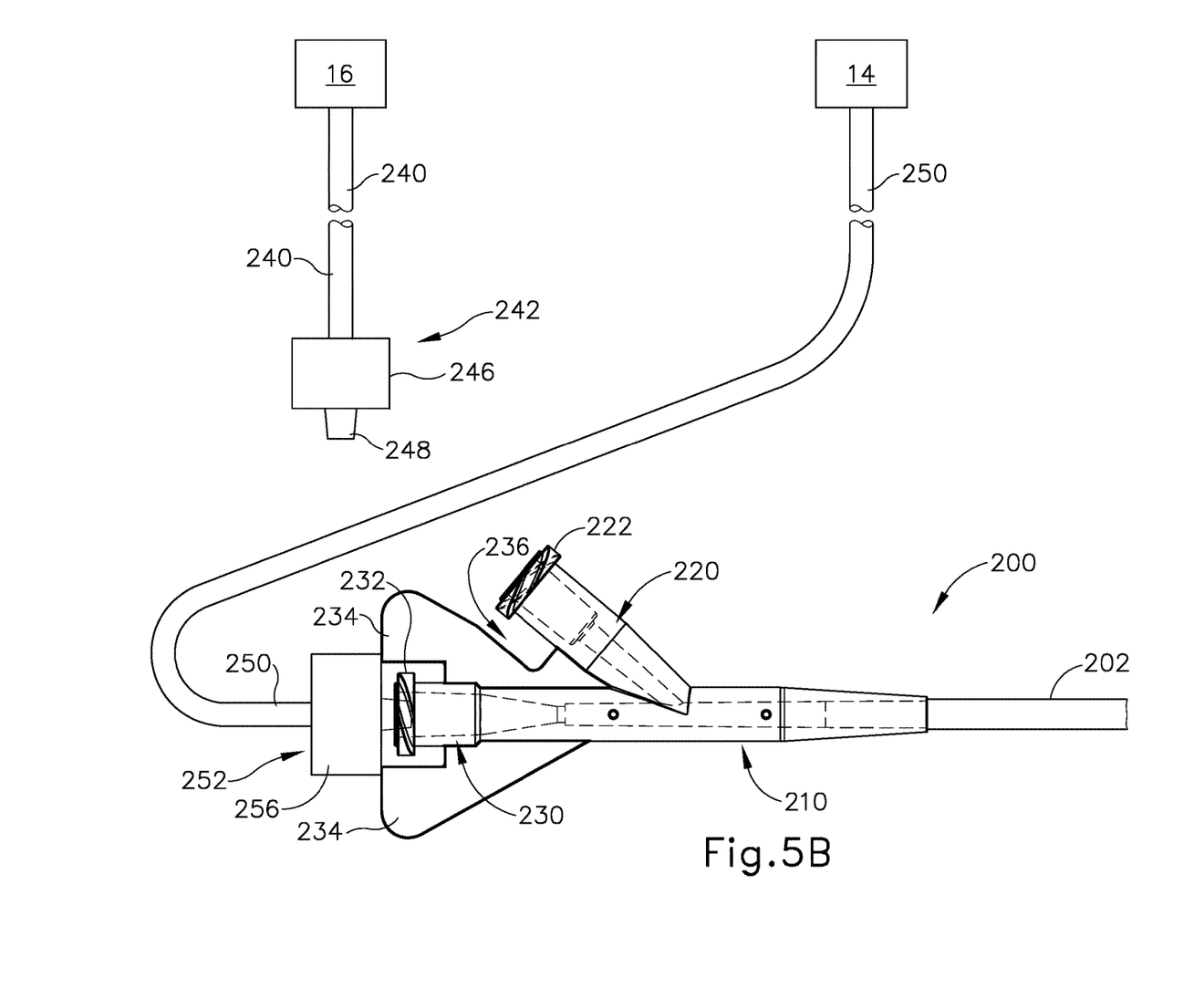
FIG. 5B depicts a top plan view of the dilation catheter of FIG. 5A, with the irrigation fluid source fitting decoupled from the fluid fitting member of the dilation catheter, and with the inflation fluid source fitting failing to couple with an irrigation fluid port of the fluid fitting member of the dilation catheter.
Figure 5C:
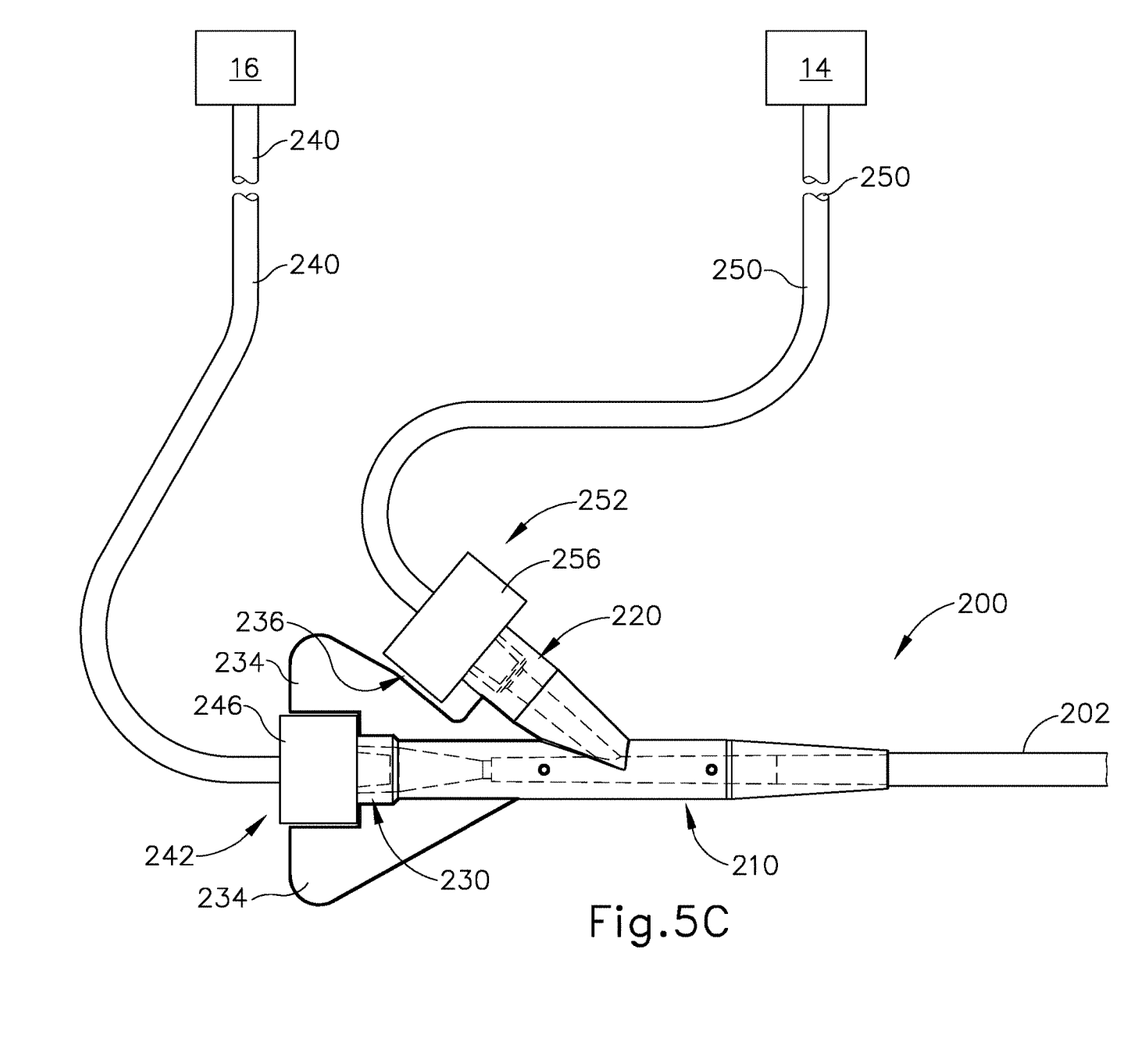
FIG. 5C depicts a top plan view of the dilation catheter of FIG. 5A, with the irrigation fluid source fitting coupled with an irrigation fluid port of the fluid fitting member of the dilation catheter, and with the inflation fluid source fitting coupled with an inflation fluid port of the fluid fitting member of the dilation catheter.

FIGS. 5A-5C show an exemplary dilation catheter (200) that is capable of providing dilation and irrigation, with conventional luer fittings, without the risk of an operator mistakenly coupling the wrong fluid source with the wrong fluid port. Dilation catheter (200) may be readily used in instrument (20) in place of dilation catheters (40, 100) described above. Dilation catheter (200) of the present example comprises a shaft (202) and a fluid fitting member (210) at the proximal end of shaft (202). While only the proximal end of dilation catheter (200) is shown in FIGS. 5A-5C, the distal end of dilation catheter (200) may be configured and operable just like the distal end of dilation catheter (100). Dilation catheter (200) may thus include a dilation balloon (e.g., like balloon (104)) and an irrigation tip (e.g., like irrigation tip (106)). Shaft (202) may also be configured and operable like shaft (102), such that shaft (202) may include separate, isolated lumens for inflation and irrigation. A proximal portion of shaft (202) may also optionally include a separate guidewire lumen that eventually merges with the irrigation lumen. Alternatively, an irrigation lumen may be used to receive a guidewire (30) along the entire length of shaft (202), such that no separate guidewire lumen is positioned anywhere along shaft (202).

Fluid fitting member (210) of the present example has a Y shape, though alternative versions may have a T shape or any other suitable shape. Fluid fitting member (210) comprises an inflation fluid port (220) and an irrigation fluid port (230). Inflation fluid port (220) includes a conventional luer threading (222). Irrigation fluid port (230) also includes a conventional luer threading (232). Fluid fitting member further includes a pair of integral wings (234) adjacent to irrigation fluid port (230). Wings (234) are rigid structures that define a gap (238) surrounding irrigation fluid port (230). Gap (238) has a width ($w_1$), as shown in FIG. 5A. Wings (234) also extend proximally relative to luer threading (232), such that luer threading (232) is positioned in gap (238) defined by wings (234). One wing (234) also defines a notch (236) adjacent to inflation fluid port (220).

As also shown in FIGS. 5A-5C, irrigation fluid source (16) is coupled with a male luer fitting (242) via a flexible conduit (240). Fitting (242) includes a head (246) and a distally projecting portion (248). Head (246) includes an internal luer threading (not shown). As shown in FIG. 5A, head (246) has a width ($w_2$). Inflation fluid source (14) is coupled with a male luer fitting (252) via a flexible conduit (250). Fitting (252) includes a head (256) and a distally projecting portion (258). Head (256) includes an internal luer threading (not shown). As shown in FIG. 5A, head (256) has a width ($w_3$).

In the present example, width ($w_3$) is greater than width ($w_1$); while width ($w_2$) is less than width ($w_1$). Thus, when an operator attempts to couple luer fitting (252) from inflation fluid source (14) with irrigation fluid port (230), head (256) will abut wings (234) such that wings (234) prevent luer fitting (252) from coupling with irrigation fluid port (230) as shown in FIG. 5B. In other words, wings (234) physically obstruct luer fitting (252) from coupling with irrigation fluid port (230). Wings (234) thus prevent the operator from mistakenly coupling irrigation fluid port (230) with inflation fluid source (14). To the extent that a portion of distally projecting portion (258) of luer fitting (252) reaches irrigation fluid port (230), head (256) is unable to reach luer threading (232) of irrigation fluid port (230). The operator is thus provided with tactile and visual feedback indicating that the operator is attempting to couple the wrong fluid source (14) with the wrong fluid port (230). The operator should therefore realize that fluid sources (14, 16) are not properly coupled with fluid fitting member (210), even if the operator successfully (albeit mistakenly) coupled luer fitting (242) with inflation fluid port (220) before the failed attempt at coupling luer fitting (252) with irrigation fluid port (230).

FIG. 5C shows luer fittings (242, 252) properly coupled with their respective ports (230, 220). As shown, gap (238) accommodates head (246) to allow the threading of head (246) to fully couple with threading (232) of irrigation fluid port (230), due to width ($w_2$) being smaller than width ($w_1$). Notch (236) is also large enough to accommodate a portion of head (256) to allow the threading of head (256) to fully couple with threading (222) of inflation fluid port (220). Thus, in the state shown in FIG. 5C, inflation fluid port (220) is properly in fluid communication with inflation fluid source (14), thereby placing inflation fluid source (14) in fluid communication with the associated inflation lumen of shaft (202); and irrigation fluid port (230) is properly in fluid communication with irrigation fluid source (16), thereby placing irrigation fluid source (16) in fluid communication with the associated irrigation lumen of shaft (202).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) an elongate shaft, wherein the elongate shaft comprises: (i) an inflation lumen, (ii) an irrigation lumen, wherein the irrigation lumen is in fluid isolation from the inflation lumen, and (iii) at least one irrigation opening at a distal portion of the shaft, wherein the at least one irrigation opening is in fluid communication with the irrigation lumen; (b) a dilation balloon located at the distal portion of the shaft, wherein the dilation balloon is in fluid communication with the inflation lumen; and (c) a fitting member at a proximal end of the shaft, wherein the fitting member comprises: (i) an inflation fluid port in fluid communication with the inflation lumen, (ii) an irrigation fluid port in fluid communication with the irrigation lumen, and (iii) a blocking structure adjacent to the irrigation fluid port, wherein the blocking structure defines a gap around the irrigation fluid port, wherein the gap has a first width.

Example 2

The apparatus of Example 1, wherein the blocking structure comprises a pair of wings.

Example 3

The apparatus of Example 2, wherein the wings are rigid.

Example 4

The apparatus of any one or more of Examples 2 through 3, wherein the wings extend proximally past a proximal end of the irrigation fluid port.

Example 5

The apparatus of any one or more of Examples 1 through 4, wherein the blocking structure further defines a notch adjacent to the inflation fluid port.

Example 6

The apparatus of any one or more of Examples 1 through 5, wherein the shaft defines a longitudinal axis, wherein the irrigation fluid port is coaxially aligned with the longitudinal axis.

Example 7

The apparatus of Example 6, wherein the inflation fluid port is obliquely oriented relative to the longitudinal axis.

Example 8

The apparatus of any one or more of Examples 1 through 7, wherein the inflation fluid port comprises a luer fitting, wherein the irrigation fluid port comprises a luer fitting.

Example 9

The apparatus of Example 8, wherein the inflation fluid port comprises a female luer fitting, wherein the irrigation fluid port comprises a female luer fitting.

Example 10

The apparatus of any one or more of Examples 1 through 9, further comprising: (a) an irrigation fluid source; (b) an irrigation fluid conduit in fluid communication with the irrigation fluid source; (c) an irrigation fluid fitting in fluid communication with the irrigation fluid conduit, wherein the irrigation fluid fitting is configured to couple with the irrigation fluid port; (d) an inflation fluid source; (e) an inflation fluid conduit in fluid communication with the inflation fluid source; and (f) an inflation fluid fitting in fluid communication with the inflation fluid conduit, wherein the inflation fluid fitting is configured to couple with the inflation fluid port.

Example 11

The apparatus of Example 10, wherein the irrigation fluid fitting has a head, wherein the head of the irrigation fluid fitting has a second width, wherein the second width is less than the first width.

Example 12

The apparatus of Example 11, wherein the inflation fluid fitting has a head, wherein the head of the inflation fluid fitting has a third width, wherein the third width is greater than the first width.

Example 13

The apparatus of any one or more of Examples 1 through 12, wherein the shaft further comprises a guidewire lumen configured to receive a guidewire.

Example 14

The apparatus of Example 13, wherein the guidewire lumen merges with the irrigation lumen.

Example 15

The apparatus of any one or more of Examples 1 through 14, wherein the at least one irrigation opening comprises a distally-facing opening, wherein the distally-facing opening is coaxially aligned with a longitudinal axis of the shaft.

Example 16

The apparatus of any one or more of Examples 1 through 15, wherein the at least one irrigation opening comprises one or more laterally-facing openings, wherein the one or more laterally-facing openings are oriented transversely relative to a longitudinal axis of the shaft.

Example 17

The apparatus of any one or more of Examples 1 through 16, wherein the dilation balloon is proximal to the at least one irrigation opening.

Example 18

A dilation system comprising: (a) an irrigation fluid source having an irrigation fluid fitting; (b) an inflation fluid source having an inflation fluid fitting; and (c) a dilation catheter, the dilation catheter comprising: (i) an elongate shaft, wherein the elongate shaft comprises: (A) an inflation lumen, (B) an irrigation lumen, wherein the irrigation lumen is in fluid isolation from the inflation lumen, and (C) at least one irrigation opening at a distal portion of the shaft, wherein the at least one irrigation opening is in fluid communication with the irrigation lumen, (ii) a dilation balloon located at the distal portion of the shaft, wherein the dilation balloon is in fluid communication with the inflation lumen, and (iii) a fitting member at a proximal end of the shaft, wherein the fitting member comprises: (A) an inflation fluid port in fluid communication with the inflation lumen, wherein the inflation fluid port is configured to couple with the inflation fluid fitting of the inflation fluid source, (B) an irrigation fluid port in fluid communication with the irrigation lumen, wherein the irrigation fluid port is configured to couple with the irrigation fluid fitting of the irrigation fluid source, and (C) a blocking structure adjacent to the irrigation fluid port, wherein the blocking structure is configured to prevent the inflation fluid fitting from coupling with the irrigation fluid port yet permit the irrigation fluid fitting to couple with the irrigation fluid port.

Example 19

The apparatus of Example 18, wherein the blocking structure defines a gap around the irrigation fluid port, wherein the inflation fluid fitting is too large to fit in the gap, wherein the irrigation fluid fitting is small enough to fit in the gap.

Example 20

An apparatus comprising: (a) an elongate shaft, wherein the elongate shaft comprises: (i) an inflation lumen, (ii) an irrigation lumen, wherein the irrigation lumen is in fluid isolation from the inflation lumen, and (iii) at least one irrigation opening at a distal portion of the shaft, wherein the at least one irrigation opening is in fluid communication with the irrigation lumen; (b) a dilation balloon located at the distal portion of the shaft, wherein the dilation balloon is in fluid communication with the inflation lumen; and (c) a fitting member at a proximal end of the shaft, wherein the fitting member comprises: (i) an inflation fluid port in fluid communication with the inflation lumen, (ii) an irrigation fluid port in fluid communication with the irrigation lumen, and (iii) a first wing extending along a first side of the irrigation fluid port, wherein the first wing extends proximally past a proximal end of the irrigation fluid port, and (iv) a second wing extending along a second side of the irrigation fluid port, wherein the second wing extends proximally past a proximal end of the irrigation fluid port, wherein the first and second wings together define a gap around the irrigation fluid port.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) an irrigation fluid source including an irrigation fluid fitting, wherein the irrigation fluid fitting has a head, wherein the head of the irrigation fluid fitting has a first width;
(b) an inflation fluid source including an inflation fluid fitting, wherein the inflation fluid fitting has a head, wherein the head of the inflation fluid fitting has a second width;
(c) an elongate shaft, wherein the elongate shaft comprises:
(i) an inflation lumen,
(ii) an irrigation lumen, wherein the irrigation lumen is in fluid isolation from the inflation lumen, and

(iii) at least one irrigation opening at a distal portion of the elongate shaft, wherein the at least one irrigation opening is in fluid communication with the irrigation lumen;
(d) a dilation balloon located at the distal portion of the elongate shaft, wherein the dilation balloon is in fluid communication with the inflation lumen; and
(e) a fitting member at a proximal end of the elongate shaft, wherein the fitting member comprises:
(i) an inflation fluid port in fluid communication with the inflation lumen,
(ii) an irrigation fluid port in fluid communication with the irrigation lumen, wherein the irrigation fluid port includes a locking structure configured to couple with the irrigation fluid fitting, and
(iii) a blocking structure adjacent to the irrigation fluid port, wherein the blocking structure defines a gap about the irrigation fluid port, wherein the gap has a third width, wherein the first width of the head of the irrigation fluid fitting is less than the third width, wherein the second width of the head of the inflation fluid fitting is greater than the third width, wherein the blocking structure includes first and second wings that each extend distally beyond the locking structure of the irrigation fluid port and proximally beyond the locking structure of the irrigation fluid port.

2. The apparatus of claim 1, wherein the first and second wings are rigid.

3. The apparatus of claim 1, wherein the elongate shaft defines a longitudinal axis, wherein the irrigation fluid port is coaxially aligned with the longitudinal axis.

4. The apparatus of claim 3, wherein the inflation fluid port is obliquely oriented relative to the longitudinal axis.

5. The apparatus of claim 1, wherein the elongate shaft further comprises a guidewire lumen configured to receive a guidewire.

6. The apparatus of claim 1, wherein the at least one irrigation opening comprises a distally-facing opening, wherein the distally-facing opening is coaxially aligned with a longitudinal axis of the elongate shaft.

7. The apparatus of claim 1, wherein the at least one irrigation opening comprises one or more laterally-facing openings, wherein the one or more laterally-facing openings are oriented transversely relative to a longitudinal axis of the elongate shaft.

8. The apparatus of claim 1, wherein the first wing includes a notch positioned between the inflation fluid port and the irrigation fluid port, wherein the notch is formed as a detent of the first wing.

9. The apparatus of claim 1, wherein the first wing extends between the inflation fluid port and the irrigation fluid port, wherein the locking structure of the irrigation fluid port extends between the first and second wings.

10. The apparatus of claim 1, wherein the locking structure includes a luer fitting, wherein the irrigation fluid port includes a luer fitting.

11. The apparatus of claim 1, wherein the locking structure of the irrigation fluid port includes a luer fitting configured to couple with a luer fitting of the irrigation fluid fitting.

12. A dilation system comprising:
(a) an irrigation fluid source having an irrigation fluid fitting, wherein the irrigation fluid fitting has a head, wherein the head of the irrigation fluid fitting has a first width;
(b) an inflation fluid source having an inflation fluid fitting, wherein the inflation fluid fitting has a head, wherein the head of the inflation fluid fitting has a second width, wherein the second width is greater than the first width; and
(c) a dilation catheter, the dilation catheter comprising:
(i) an elongate shaft, wherein the elongate shaft comprises:
(A) an inflation lumen,
(B) an irrigation lumen, wherein the irrigation lumen is in fluid isolation from the inflation lumen, and
(C) at least one irrigation opening at a distal portion of the elongate shaft, wherein the at least one irrigation opening is in fluid communication with the irrigation lumen,
(ii) a dilation balloon located at the distal portion of the elongate shaft, wherein the dilation balloon is in fluid communication with the inflation lumen, and
(iii) a fitting member at a proximal end of the elongate shaft, wherein the fitting member comprises:
(A) an inflation fluid port in fluid communication with the inflation lumen, wherein the inflation fluid port is configured to couple with the inflation fluid fitting of the inflation fluid source,
(B) an irrigation fluid port in fluid communication with the irrigation lumen, wherein the irrigation fluid port is configured to couple with the irrigation fluid fitting of the irrigation fluid source, and
(C) a blocking structure adjacent to the irrigation fluid port, wherein the blocking structure includes at least one wing that extends distally beyond the irrigation fluid port and proximally beyond the irrigation fluid port, wherein the at least one wing of the blocking structure is configured to prevent the head of the inflation fluid fitting from coupling with the irrigation fluid port yet permit the head of the irrigation fluid fitting to couple with the irrigation fluid port.

13. The dilation system of claim 12, wherein the at least one wing extends between the inflation fluid port and the irrigation fluid port.

14. The dilation system of claim 12, wherein the irrigation fluid port includes a locking structure configured to couple with the irrigation fluid fitting, wherein the at least one wing includes first and second wings that each extend distally beyond the locking structure of the irrigation fluid port and proximally beyond the locking structure of the irrigation fluid port.

15. An apparatus comprising:
(a) an irrigation fluid source including an irrigation fluid fitting, wherein the irrigation fluid fitting has a head, wherein the head of the irrigation fluid fitting has a first width;
(b) an inflation fluid source including an inflation fluid fitting, wherein the inflation fluid fitting has a head, wherein the head of the inflation fluid fitting has a second width that is greater than the first width;
(c) an elongate shaft, wherein the elongate shaft comprises:
(i) an inflation lumen,
(ii) an irrigation lumen, wherein the irrigation lumen is in fluid isolation from the inflation lumen, and (iii) at least one irrigation opening at a distal portion of the elongate shaft, wherein the at least one irrigation opening is in fluid communication with the irrigation lumen;

(d) a dilation balloon located at the distal portion of the elongate shaft, wherein the dilation balloon is in fluid communication with the inflation lumen; and
(e) a fitting member at a proximal end of the elongate shaft, wherein the fitting member comprises:
   (i) an inflation fluid port in fluid communication with the inflation lumen,
   (ii) an irrigation fluid port in fluid communication with the irrigation lumen, wherein the irrigation fluid port includes a locking structure,
   (iii) a first wing extending along a first side of the irrigation fluid port, wherein the first wing extends proximally pasta proximal end of the locking structure of the irrigation fluid port, wherein the first wing includes a notch positioned between the inflation fluid port and the irrigation fluid port and is formed as a detent of the first wing, wherein the notch is configured to accommodate a portion of the inflation fluid fitting, and
   (iv) a second wing extending along a second side of the irrigation fluid port, wherein the second wing extends proximally past the proximal end of the irrigation fluid port,
wherein the first and second wings together define a gap about the locking structure of the irrigation fluid port that is configured to couple with the irrigation fluid fitting,
wherein the first and second wings are configured to prevent the inflation fluid fitting from coupling with the irrigation fluid port yet permit the irrigation fluid fitting to couple with the irrigation fluid port.

16. The apparatus of claim 15, wherein the fitting member defines a longitudinal axis, wherein the first and second wings each extend distally along the longitudinal axis beyond the locking structure of the irrigation fluid port and proximally along the longitudinal axis beyond the locking structure of the irrigation fluid port.

* * * * *